(12) United States Patent
O'Day et al.

(10) Patent No.: US 8,568,369 B2
(45) Date of Patent: Oct. 29, 2013

(54) INFUSION CATHETER AND METHOD

(75) Inventors: Therese O'Day, Bloomington, IN (US); Richard Earl Luedemann, Ellettsville, IN (US); Shyam Kuppurathanam, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 183 days.

(21) Appl. No.: 12/851,005

(22) Filed: Aug. 5, 2010

(65) Prior Publication Data

US 2012/0035586 A1 Feb. 9, 2012

(51) Int. Cl.
*A61M 25/00* (2006.01)
*A61M 5/00* (2006.01)

(52) U.S. Cl.
USPC .......................... 604/246; 604/526

(58) Field of Classification Search
USPC ................ 604/526, 103.01, 30, 246
See application file for complete search history.

(56) References Cited

U.S. PATENT DOCUMENTS

| | | |
|---|---|---|
| 5,269,755 A | 12/1993 | Bodicky |
| 5,462,523 A * | 10/1995 | Samson et al. .......... 604/30 |
| 5,653,689 A | 8/1997 | Buelna et al. |
| 5,769,884 A | 6/1998 | Solovay |
| 5,782,811 A * | 7/1998 | Samson et al. .......... 604/527 |
| 6,197,014 B1 | 3/2001 | Samson et al. |
| 6,350,253 B1 | 2/2002 | Deniega et al. |
| 6,929,626 B2 * | 8/2005 | DiCarlo et al. .......... 604/249 |
| 7,004,923 B2 | 2/2006 | Deniega et al. |
| 2009/0157164 A1 | 6/2009 | McKinsey et al. |

* cited by examiner

*Primary Examiner* — Kevin C Sirmons
*Assistant Examiner* — Bradley Osinski
(74) *Attorney, Agent, or Firm* — Liell & McNeil (57) ABSTRACT

An infusion catheter includes an elongate catheter body having a proximal body component and a distal body component. The distal body component includes a distal body outer surface and a distal body inner surface defining an infusion lumen. The distal body component further includes a skeleton, and a porous infusion control textile contacting the skeleton and extending circumferentially about a longitudinal axis of the catheter and defining a fluid emission profile thereof. The porous infusion control textile further includes a fiber network having a higher density space filling configuration at a proximal textile end and a lower density space filling configuration at a distal textile end, and defining a pressure sensitive flow rate property and a pressure insensitive flow distribution property of the fluid emission profile.

11 Claims, 4 Drawing Sheets

INFUSION CATHETER AND METHOD

TECHNICAL FIELD

The present disclosure relates generally to strategies for conveying a treatment fluid to a body lumen of a patient, and relates more particularly to controlling fluid flow distribution from an infusion catheter by way of a porous infusion control textile.

BACKGROUND

In the field of peripheral intervention, devices known as infusion catheters are commonly used to deliver a therapeutic treatment fluid to an intraluminal treatment site within a body lumen, such as a vein or artery. One general class of infusion catheters utilizes a longitudinally extending passage which fluidly connects a supply of treatment fluid located outside of the patient with the treatment site by way of ports formed in a body of the infusion catheter. A typical infusion procedure involves leaving an infusion catheter within a patient for a period of time while treatment fluid flows from the fluid supply into the infusion catheter, and thenceforth into the body lumen. One common application of infusion catheters is the treatment of clots or other undesired tissues which have formed within a vein or artery. Treatment fluids commonly referred to as thrombolytic agents are often used to dissolve clot material.

While various infusion techniques have been used for many years, they are not without shortcomings. Basic assumptions about the operation and behavior of infusion catheters while resident in a vein or artery, for example, may not always be true. For instance, it is often assumed that all portions of an infusion length of an infusion catheter will predictably, reliably and uniformly infuse fluid into the treatment site throughout the entire course of an infusion procedure. In some instances, however, portions of an infusion catheter and, notably, more distal portions, may actually be supplying little or no treatment fluid. This phenomenon is believed to result at least in part from the loss in pressure of the treatment fluid as it flows in a proximal to distal direction through the infusion catheter. When the treatment fluid arrives at a distal region of an infusion catheter, there may be insufficient pressure for the treatment fluid to overcome a fluid pressure such as a pressure of blood within the body lumen to be treated. As a result, infusion procedures may be ineffective, require undue lengths of time, or have other shortcomings such as the oversupply of treatment fluid to compensate for non-uniformity in distribution.

Clinicians have experimented with various strategies for improving uniformity of treatment fluid distribution from an infusion catheter. One known strategy is to provide a non-uniform distribution of infusion ports in the catheter body, with the infusion ports being relatively few in number in a proximal portion of an infusion catheter and relatively great in number in a distal portion. This strategy is believed to at least somewhat overcome the problems associated with fluid pressure loss noted above. Other strategies include configuring an infusion catheter such that all or part of the infusion length of the catheter functions as a valve. This technique allows fluid pressure to build within the infusion catheter, and then actuate the valve to provide a burst of treatment fluid into the body lumen which is believed to be relatively uniform. While these and other techniques have met with some success, there remains room for improvement.

SUMMARY OF THE DISCLOSURE

In one aspect, an infusion catheter includes an elongate catheter body defining a longitudinal axis extending between a proximal body component and a distal body component. The proximal body component includes a proximal body outer surface and a proximal body inner surface, and the distal body component includes a distal body outer surface, a distal body inner surface, and a tapered distal tip. The proximal body inner surface defines a fluid supply lumen extending between a supply lumen inlet and a supply lumen outlet, and the distal body inner surface defines an infusion lumen connecting with the fluid supply lumen and extending between an infusion lumen inlet and a plurality of infusion lumen outlets formed in the distal body outer surface. The distal body component further includes a skeleton, and a porous infusion control textile contacting the skeleton and including the plurality of infusion lumen outlets. The porous infusion control textile extends circumferentially about the longitudinal axis and defines a fluid emission profile of the infusion catheter. The porous infusion control textile further includes a fiber network extending between a proximal textile end and a distal textile end, the fiber network having a higher density space filling configuration at the proximal textile end and a lower density space filling configuration at the distal textile end, and defines a pressure sensitive flow rate property and a pressure insensitive flow distribution property, of the fluid emission profile.

In another aspect, a method of performing an infusion procedure on a patient includes supplying a treatment fluid from a proximal fluid supply lumen to a distal infusion lumen of an infusion catheter, and conveying the treatment fluid from the infusion lumen into a body lumen of a patient. The method further includes controlling a flow rate of the treatment fluid during the conveying step in a manner which is responsive to a supply pressure of the treatment fluid. The method further includes reducing non-uniformity in a flow distribution pattern of the treatment fluid during the conveying step in a manner which is decoupled from the supply pressure, at least in part by passing the treatment fluid through a textile fiber network filling a distally decreasing proportion of a space between an outer surface and an inner surface of the infusion catheter.

DETAILED DESCRIPTION

Figure 1:
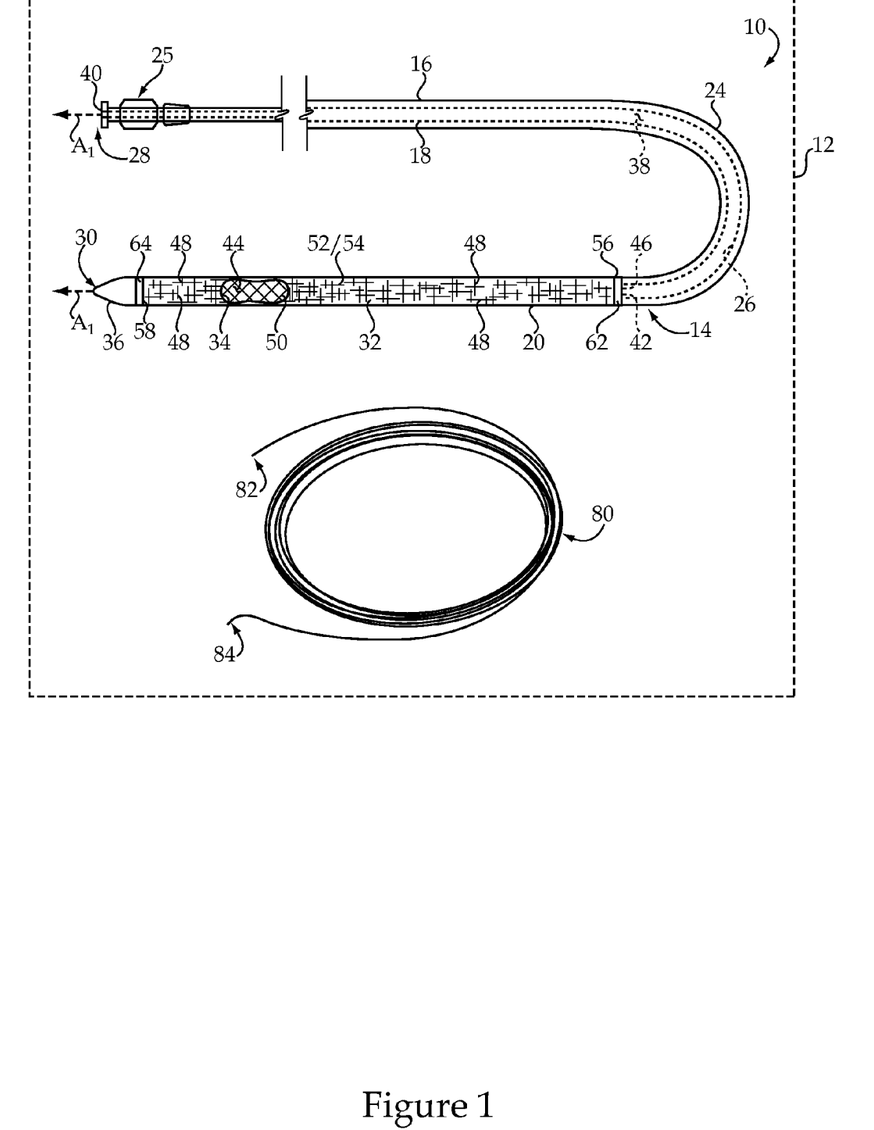
FIG. 1 is a side diagrammatic view of an infusion mechanism, according to one embodiment.

Referring to FIG. 1, there is shown an infusion mechanism 10 which may be used for treating an intraluminal site in a patient. Infusion mechanism 10 may include an infusion catheter 14, and a wire guide 80, catheter 14 and wire guide 80 being positioned within a sterile package 12. Sterile package 12 may include a sealed, peel-open pouch in one embodiment. Other packaging features such as a tube protector coil as well as other infusion mechanism components such as adapters and fittings, or additional wire guides may be included but are omitted from FIG. 1. As will be further apparent from the following description, infusion mechanism 10 may uniquely adapted to address certain challenges relating to controlling a flow of a treatment fluid into a body lumen of a patient during an infusion procedure.

Wire guide 80 may include a proximal wire guide tip 82 and a distal wire guide tip 84. Wire guide 80 may be relatively soft or floppy in a region adjacent distal tip 84 in a manner well known in the art. As further described herein, wire guide 80 may be used in guiding catheter 14 to a treatment site within a patient. In one embodiment, catheter 14 may be configured for passing over wire guide 80, and could be configured as a rapid exchange catheter in certain embodiments. Rather than over-the-wire placement, catheters contemplated herein might be placed by any of a variety of other placement methods such as by way of the use of a placement sheath or the like. In certain embodiments, wire guide 80 might serve functions beyond guiding/placement of catheter 14, such as blocking a distal opening in catheter 14 by way of an occlusion bulb positioned adjacent distal tip 84, as further explained herein.

Infusion catheter 14 may include an elongate catheter body 16 defining a longitudinal axis $A_1$ extending between a proximal body component 18 and a distal body component 20. Proximal body component 18 may include a proximal body outer surface 24 and a proximal body inner surface 26. Distal body component 20 may include a distal body outer surface 32, a distal body inner surface 34, and a tapered distal tip 36. Catheter body 16 may further include a proximal body end 28 and a distal body end 30. A manifold 25 or the like may be positioned at or coupled with proximal body end 28 for connecting with components used to supply a treatment fluid to catheter 14 as further described herein.

Inner surface 26 may define a fluid supply lumen 38 extending between a supply lumen inlet 40 located at proximal end 28 and a supply lumen outlet 42. Inner surface 34 of distal body component 20 may define an infusion lumen 44 connecting with fluid supply lumen 38 at supply lumen outlet 42 and extending between an infusion lumen inlet 46 and a plurality of infusion lumen outlets 48 formed in outer surface 32.

Distal body component 20 may further include a skeleton 50, and a porous infusion control textile 52 contacting skeleton 50 and including outlets 48. Textile 52 may extend circumferentially about longitudinal axis $A_1$ and defines a fluid emission profile of catheter 14. Textile 52 may further include a fiber network 54 extending between a proximal textile end 56 and a distal textile end 58. A first seal assembly 62 may be located between body component 18 and body component 20, and a second seal assembly 64 may be located between body component 20 and profiled distal tip 36. Seal assemblies 62 and 64 may be positioned adjacent to textile ends 56 and 58, respectively, or textile ends 56 and 58 might be positioned within seal assemblies 56 and 58. Example construction of seal assemblies 62 and 64 is further described below. Radiopaque markers (not shown) may be positioned adjacent to, within, or near seal assemblies 62 and 64 in one embodiment, to indicate an approximate infusion length of catheter 14 which extends in an axial direction from approximately first seal assembly 62 to approximately second seal assembly 64.

Figures 2, 3, 4, 5:
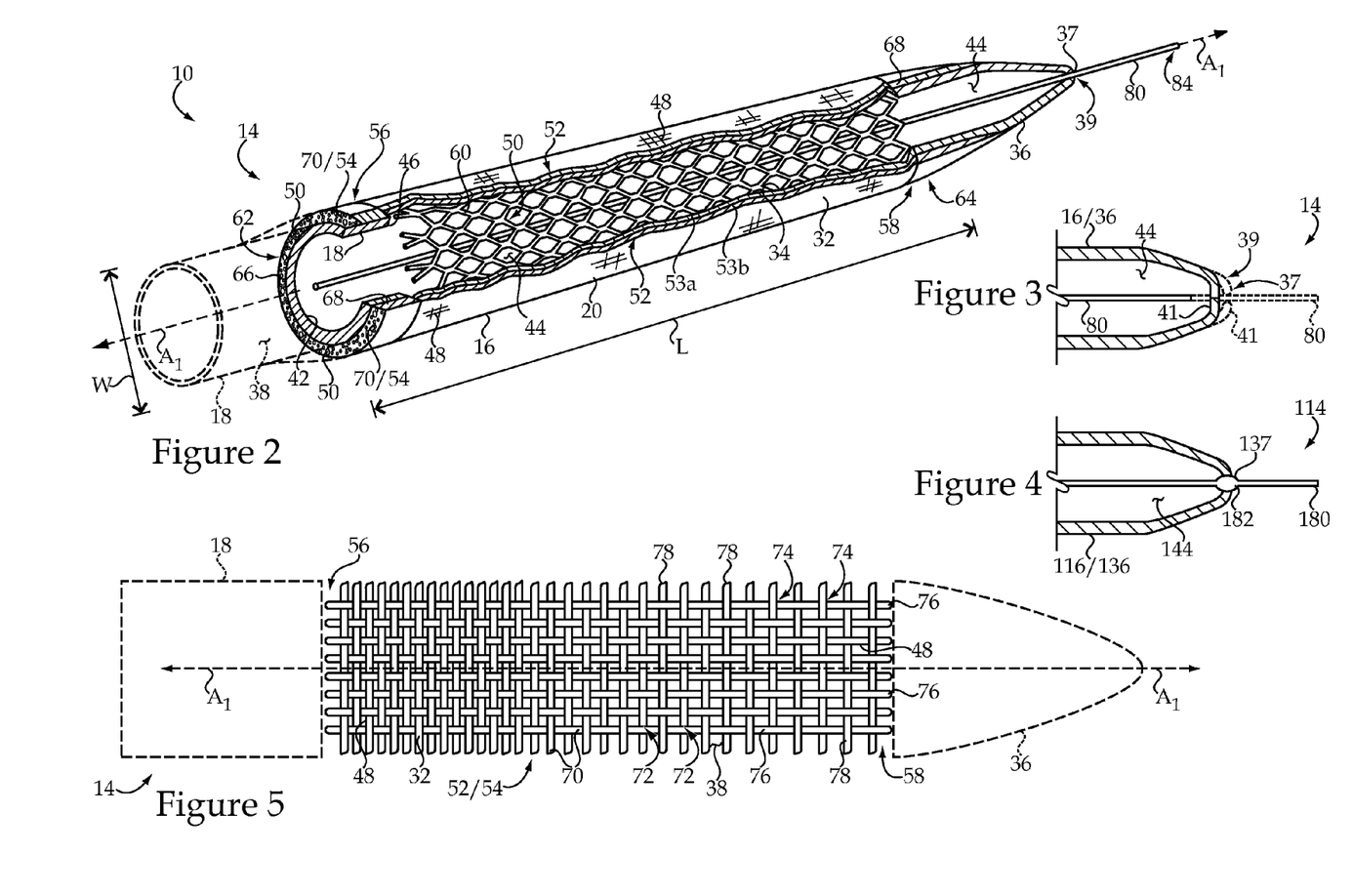
FIG. 2 is a partially sectioned perspective view, in two section planes, of a portion of the infusion mechanism of FIG. 1.
FIG. 3 is a sectioned side diagrammatic view of a portion of the infusion mechanism of FIG. 1.
FIG. 4 is a sectioned side diagrammatic view of a portion of an infusion mechanism, according to another embodiment.
FIG. 5 is a pictorial view of a porous infusion control textile according to one embodiment.

Referring now also to FIG. 2, there is shown a perspective view in two section planes of infusion mechanism 10 as it might appear having wire guide 80 extending axially therethrough and aligned with longitudinal axis $A_1$. It may be noted that wire guide 80 extends in a distal direction from tip 36. In the embodiment shown, wire guide 80 extends through a distal outlet 37 formed in tip 36. Catheter 14 may also include a valve mechanism 39 positioned at distal outlet 37. Valve mechanism 39 may include an open state, as shown, and a closed state. Passing wire guide 80 through valve mechanism 39 can adjust valve mechanism 39 from its closed state to its open state. Valve mechanism 39 may be biased towards a closed state such that it blocks or substantially blocks distal outlet 37 when wire guide 80 is not positioned therein. This can enable fluid supplied into lumen 38 to pass out of outlets 48, but be inhibited from passing out of distal outlet 37, for reasons which will be apparent from the following description.

Referring to FIG. 3, there is shown a sectioned side diagrammatic view of tip 36 illustrating valve mechanism 39 in its closed state, and also illustrating valve mechanism 39 in its open state in phantom. Wire guide 80 is also shown at a first position, retracted from distal outlet 37 and valve mechanism 39, and at an advanced position in phantom. In one embodiment, valve mechanism 39 may include a plurality of resilient, deformable flaps 41 which are biased toward a radially inward position at which flaps 41 abut, or nearly abut, one another and thereby close outlet 37. When wire guide 80 is advanced through outlet 37, flaps 41 may be urged towards distally advanced and radially outward positions to allow the passage of wire guide 80 therethrough. When wire guide 80 is at the first, retracted position, flaps 41 may tend to assume a rest state, blocking or substantially blocking outlet 37.

Referring to FIG. 4, there is shown a catheter 114 according to another embodiment. Catheter 114 may include an elongate catheter body 116 having a profiled distal tip 136 which defines a fluid outlet 137. Instead of being equipped with a valve mechanism at distal outlet 137, a wire guide 180 having an occlusion bulb 182 may be provided which can be advanced into outlet 137 or retracted to respectively block or open a lumen 144 for purposes analogous to those of valve mechanism 39. In still other embodiments, an infusion catheter according to the present disclosure may not include a distal outlet at all, such as may be the case with an infusion catheter configured to be placed via a placement sheath or the like as mentioned above.

Returning to FIG. 2, it will be recalled that textile 52 may extend circumferentially about longitudinal axis $A_1$. In one embodiment, textile 52 may include one or more textile layers 53a, 53b each having a tubular configuration and being wrapped about skeleton 50, and extending at least one complete circumferential turn about longitudinal axis $A_1$. It will further be recalled that a plurality of infusion lumen outlets 48 may be formed in outer surface 32. Catheter 14 may include a total of one infusion lumen 44 in simultaneous fluid communication with all of outlets 48. Lumen 44 may thus include a common infusion lumen adapted to simultaneously supply a treatment fluid to each of outlets 48 for infusing the treatment fluid into a body lumen of a patient. The use of a common infusion lumen 44, in contrast to multiple separate lumens, is contemplated to provide one practical implementation strategy. While the present disclosure is not strictly limited to a single infusion lumen design, multiple different infusion lumens which each fluidly communicate with a different subset of outlets of an infusion catheter would not include a common infusion lumen as contemplated herein.

Also shown in FIG. 2 are additional example features of seal assemblies 62 and 64. In one embodiment, seal assemblies 62 and 64 may include a first bushing 66 and a second bushing 68, respectively. Portions of textile 52 and skeleton 50 may be sandwiched between first bushing 66 and proximal body component 18 within first seal assembly 62. Portions of textile 52 and skeleton 50 may be sandwiched between second bushing 68 and tip 36 within second seal assembly 64. Each of bushings 66 and 68 may be formed from material which is similar or identical to a material of which body component 18 and tip 36 are formed. A variety of different materials suitable for catheter body manufacture are well known in the art such as nylon, PTFE, or any of a variety of other suitable biocompatible materials. In one embodiment, seal assemblies 62 and 64 may be formed by placing textile 52 over skeleton 50, placing body component 18 and tip 36 within the textile and skeleton assembly, and then placing bushings 66 and 68 over the assembly comprised of components 18, 36, 50, and 52. Thus, an axial overlap between skeleton 50, textile 52, body component 18, and bushing 66 may be established, and a similar overlapping arrangement of tip 36, skeleton 50, textile 52, and bushing 68, may be established. In the resulting assembly, tip 36 may not yet have been shaped to final form, but alternatively could include its final tapering profile. The assembly of components 18, 36, 50, 52, 66 and 68 may then be heated, for example, at least in the regions where seal assemblies 62 and 64 are to be formed, such that material of bushings 66 and 68 and material of component 18 and tip 36 softens and melts, and is then allowed to harden and solidify to create a matrix trapping part of skeleton 50 and part of textile 52 therein, and connecting skeleton 50 and textile 52 with components 18 and 36. Melted material of bushings 66 and 68 may fuse with the material of body component 18 and the material of tip 36, resulting in a fluid seal at the two indicated seal assembly locations. A mandrel or the like might be positioned within the assembly of components 18, 36, 50, 52, 66 and 68 during manufacturing, to provide temporary structural support to the materials softened by heating, if desired It will also be recalled that textile 52 may include one or more textile layers wrapped about and contacting skeleton 50. In the embodiment shown, textile 52 may include an inner textile layer 53a, and an outer textile layer 53b. Textile layers 53a and 53b may be made simultaneously such as by weaving by way of known techniques. In one practical implementation strategy, textile layers 53a and 53b may be woven on a conventional shuttle loom. Textile layers 53a and 53b may also be attached to skeleton 50, such as by manual or machine sewing, or some other technique such as an adhesive. Textile layers 53a and 53b may further be attached to one another such as by way of sewing, or some other technique such as adhesives or heat fusion.

Textile 52 may further define a width W in a direction normal to and intersecting axis $A_1$, which may be equal to about 10.0 millimeters or less, and in certain embodiments may be equal to about 5.0 millimeters or less, or even equal to about 2.0 millimeters or less. Textile 52 may also define an infusion length L of catheter 14 extending approximately from a distal edge of seal assembly 62 to approximately a proximal edge of seal assembly 64. Length L may be equal to about 50.0 centimeters or greater, and may be equal to about 70.0 centimeters or greater in some embodiments. One example embodiment includes a generally tubular double layer textile having a width or outer diameter equal to about 2.0 millimeters and an infusion length equal to about 60.0 centimeters. Another example embodiment might include a width or outer diameter equal to about 5.0 centimeters and an infusion length equal to about 70.0 centimeters. Skeleton 50 may include an axial length similar to the infusion length of the associated textile 52, and a width or outer diameter dimension slightly less than the associated textile width, at least when catheter 14 is assembled and ready for service. The width dimension of skeleton 50 might actually be slightly larger than a width dimension of textile 52 when textile 52 is in a relaxed state and skeleton 50 is not positioned therein. Insertion of skeleton 50 into textile 52 may modestly stretch textile 52 to a final shape and configuration. As used herein, the term "about" should be understood in the context of a number of significant digits. Accordingly, about 2.0 millimeters means between 1.5 and 2.4 millimeters. About 50.0 centimeters means between 45.5 centimeters and 50.4 centimeters, and so on.

Textile 52 may be formed from any of a variety of known biocompatible yarns, including thermoplastic yarns such as nylon yarns, PTFE yarns, polyester yarns, and yarns formed from a variety of other materials. The present disclosure is not thereby limited, however, and embodiments are contemplated wherein fibrous materials other than yarns such as monofilament fibers, or non-thermoplastics are used. Still other embodiments may include metallic textiles in which metal fibers are used to form textile 52. The term "textile" is used herein consistent with its definition in the field of textile engineering, and broadly refers to any member of the general class of articles composed of fibers and produced by one or more of the techniques of weaving, knitting, braiding, felting, or any other known textile manufacturing technique.

In the embodiment shown, skeleton 50 includes an endoskeleton formed from a plurality of metallic wires 60. Wires 60 may be irreversibly attached to one another by welding, soldering, or brazing, for example. Wires 60 need not be irreversibly attached to one another, however, and instead might be coupled together in a manner similar to that used to manufacture certain stents by techniques having analogies in the manufacture of textiles. For instance, wires 60 may be "woven" or "knit" to one another such that some relative sliding movement between adjoining wires is possible. Any suitable means for forming skeleton 50 may be used whereby wires 60 form a relatively rigid wire frame providing structural support to the relatively non-rigid textile 52. Configured as a wire frame skeleton, such as the endoskeleton shown, wires 60 may provide structural support to textile 52 during guiding catheter 14 to a treatment site within a patient. In still other embodiments, skeleton 50 could be formed from a tubular metallic body having holes cut therein by way of laser or some other suitable machining technique. As discussed above, skeleton 50 is part of catheter 14 and typically attached to other components of catheter 14, such as by sewing skeleton 50 to textile 52, and/or by melting bushings 66 and 68 about skeleton 50. A mechanism which includes a support device removable from a catheter assembly in vivo would not likely include a "skeleton" as that term is intended to be understood herein.

It may be desirable to make skeleton 50 from certain materials and/or having a configuration such that skeleton 50 is somewhat flexible, to facilitate passing catheter 14 through tortuous portions of a patient's anatomy, such as curves within a vascular structure. To this end, embodiments are contemplated wherein skeleton 50 comprises a stent or a portion of a stent of the type used to prop open veins or arteries in the human vasculature, and having some degree of flexibility and/or springiness. Certain stents of the type manufactured by the Assignee of the present patent application are suitable for this purpose. Example, suitable materials for wires 60 may include Nitinol®, stainless steel, platinum, metallic alloys, and other known biocompatible metallic materials. In a practical implementation strategy, skeleton 50 is formed of metallic materials, however, the present disclosure is not strictly limited and suitable elastomeric materials could also be used.

As mentioned above, textile 52 includes a porous infusion control textile defining a fluid emission profile of catheter 14. The fluid emission profile may be understood as a set of properties of catheter 14 evident when fluids are being transferred between lumen 44 and an intraluminal space such as a vein or artery via textile 52. These properties may include, for example, a flow rate property such as a total volume of fluid flow out of lumen 44 per unit of time, at a given fluid pressure within lumen 44. Another property of the fluid emission profile may include a flow distribution property, such as a relative distribution of fluid flow from textile 52 along infusion length L and/or a relative distribution of fluid flow circumferentially about longitudinal axis $A_1$, or both. In one embodiment, the fluid emission profile of catheter 14 may include a longitudinally uniform flow distribution property. The fluid emission profile may also include a circumferentially uniform flow distribution property. A porous infusion control textile defining a fluid emission profile which includes a longitudinally and circumferentially uniform flow distribution property would typically exhibit the same infusion rate or fluid flow rate regardless of where along or about the infusion length of the associated catheter the fluid flow is observed or measured.

Other embodiments are contemplated where a porous infusion control textile is configured to provide a non-uniform flow distribution property. A catheter having a non-uniform flow distribution property may exhibit different fluid flow rates at different locations along or about the infusion length. For example, where a catheter according to the present disclosure is used to infuse a thrombolytic treatment fluid it could be desirable to infuse treatment fluid from the catheter at a relatively greater flow rate or total quantity at or close to an upstream end of a thrombus, and at a relatively lesser flow rate or total quantity at or close to a downstream end of the thrombus. A flow of blood through the thrombus could assist in carrying the infused treatment fluid from the upstream end toward the downstream end, through the area to be treated. The relatively lesser amount or rate of infusion towards the downstream end of the thrombus could advantageously result in less thrombolytic fluid being carried past the thrombus and to other parts of the body. A catheter configured to include a fluid emission profile having a non-uniform flow distribution property could be used in such an application. A catheter having a flow distribution biased toward relatively greater proximal flow, or biased toward relatively greater distal flow, could be used depending upon whether the catheter is to be inserted in an upstream direction or a downstream direction into the treatment site.

The flow rate property discussed above may include a pressure sensitive flow rate property. This means that an increase or decrease in pressure within lumen 44 can be expected to result in an increase or decrease in flow or infusion rate from catheter 14 which is positively correlated with the increase or decrease in pressure, respectively. In one embodiment, fluid may be supplied to inlet 40 at a pressure which is equal to about 3 atmospheres or less, and which may be equal to about 2 atmospheres or less. By the time the supplied fluid reaches lumen 44, its pressure may be somewhat less than the supply pressure due to loss factors.

The flow distribution property discussed above may include a pressure insensitive flow distribution property. This may be understood to mean that flow distribution of treatment fluid through textile 52 is relatively unaffected by changes in a pressure of fluid in lumen 44. Stated another way, increasing or decreasing a pressure of treatment fluid within lumen 44 may be expected to have little, if any, effect on the relative distribution of fluid being effused from outlets 48. Thus, a change in fluid pressure within lumen 44 may be expected to have little, if any, effect on uniformity of flow distribution longitudinally and circumferentially about catheter 14 where textile 52 is configured for uniform flow distribution. The same would typically be true where textile 52 is configured for non-uniform flow distribution, in other words the non-uniformity of the flow distribution can be expected to be relatively stable regardless of changes in a pressure of treatment fluid within lumen 44. Those skilled in the art will of course appreciate that extreme pressures and extreme changes in pressure might be expected to induce some change in flow distribution, but such conditions are typically not expected during the ordinary course of treating a patient in an infusion procedure. For certain catheters contemplated herein, using a radiopaque die and suitable radiography equipment, a fluid pressure change in lumen 44 of about 1 atmosphere might induce an observable change in flow rate through textile 52 but induce little or no observable change in flow distribution from textile 52.

The fluid emission profile and attendant flow properties described herein result at least in part from a unique configuration of textile 52, and in particular the unique configuration of fiber network 54. Fiber network 54 may include a higher density space filling configuration at proximal textile end 56, and a lower density space filling configuration at distal textile end 58. Distal body outer surface 32 and distal body inner surface 34 may be spaced from one another, such as by a thickness of textile layers 53a and 53b. In the illustrated embodiment, catheter body 16 includes a generally tubular/cylindrical configuration of distal body component 20. Radially outermost points of outer surface 32 may define a generally cylindrical shape tangent to textile 52. Radially innermost points of inner surface 34 may also define a generally cylindrical shape in an analogous manner. The respective generally cylindrical shapes may thus be understood to define a space between them which is filled in part by fiber network 54. The proportion of the space filled by fiber network 54 may decrease in a distal direction. Accordingly, material of fiber network 54 may fill a relatively high proportion of this cylindrical space at or adjacent to proximal textile end 56, and a relatively low proportion of this space adjacent to or at distal textile end 58. Fiber network 54 may fill a moderate proportion of the space in a region of textile 52 which is about half way between ends 56 and 58. The space filling configuration of fiber network 54 may smoothly transition from higher density at proximal textile end 56 to lower density at distal textile end 58, but might also transition relatively abruptly or stepwise from higher density, to moderate density, to lower density, or via still another pattern.

In one embodiment, fiber network 54 may include a fiber pattern which includes a distally attenuated fiber crowding pattern. The higher density space filling configuration may include a relatively more tightly crowded fiber pattern, and the lower density space filling configuration may include a relatively less tightly crowded fiber pattern, whereas a middle portion of fiber network 54 may include a relatively moderately crowded fiber pattern. As used herein, the term "distally attenuated" may be understood to mean that, relative fiber crowding (i.e. an average spacing between individual fibers) decreases in a proximal to distal direction within fiber network 54. As alluded to above, a relative spacing among fibers comprising fiber network 54 may be different depending upon the particular longitudinal position along textile 52 which is observed. The relative spacing among fibers comprising fiber network 54 may further define a relative porosity of textile 52. Accordingly, in one practical implementation strategy, textile 52 may include a distally incremented porosity defined by the spacing among fibers of fiber network 54 which transitions from relatively low porosity at proximal textile end 56 to relatively high porosity at distal textile end 58.

Referring also to FIG. 5, there is shown a view of a portion of textile 52 illustrating additional features of fiber network 54 in greater detail. It may be noted that textile 52 extends from proximal end 56 adjacent body component 18 (shown in phantom) to distal textile end 58 adjacent tip 36 (shown in phantom). In the illustrated embodiment fiber network 54 includes a plurality of interlaced fibers 70 arranged an undular pattern. Each of fibers 70 may include a plurality of radially outward undulations 72, relative to axis $A_1$, which each include a portion of outer surface 32. Each of fibers 70 may further include a plurality of radially inward undulations 74, relative to axis $A_1$, which each include a portion of inner surface 34. Inner surface 34 is positioned opposite outer surface 32, and is thus hidden from view in FIG. 5. In the illustrated embodiment, textile 52 includes a plain weave woven textile. Fibers 70 further include a plurality of warp fibers 76 and a plurality of weft fibers 78. A distally attenuated fiber crowding pattern of fiber network 54 is defined in the FIG. 5 embodiment by a non-uniform crowding of warp fibers 76. Weft fibers 78 might additionally or alternatively be non-uniformly crowded. Warp fibers 76 and weft fibers 78 may each include fibers having a similar denier. In other embodiments the denier of warp fibers 76 versus weft fibers 78 might be different. Denier could also vary within individual fibers, transitioning from a higher denier at proximal end 56 to a lesser denier at distal end 58, for example.

Figure 6:
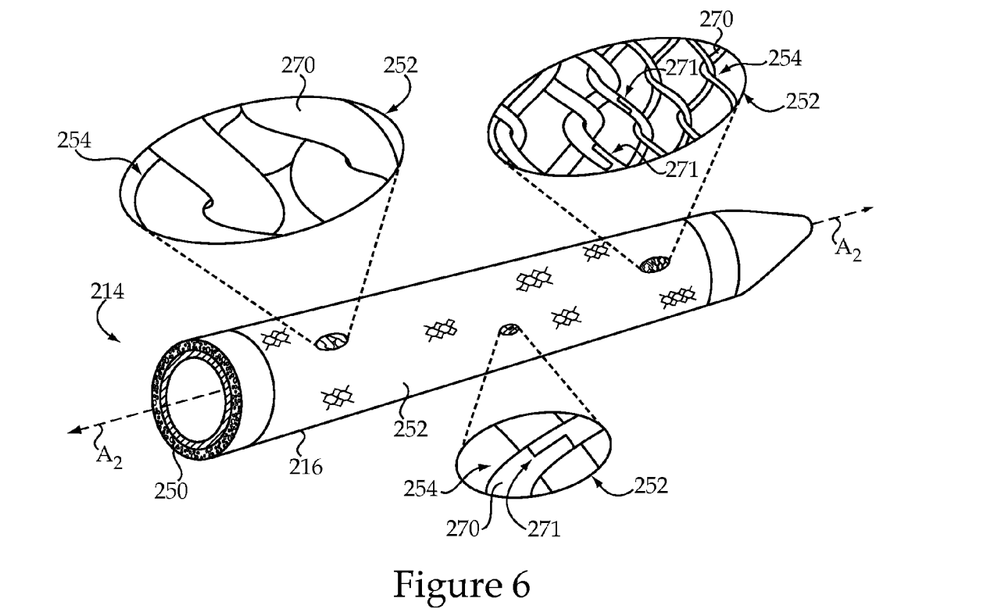
FIG. 6 is a partially sectioned perspective view, with detailed enlargements, of an infusion mechanism according to another embodiment.

Still other means for establishing differing density space filling configurations of a porous infusion control textile are contemplated herein. Turning to FIG. 6, there is shown an infusion catheter 214 according to another embodiment. Catheter 214 includes an elongate catheter body 216 having a porous infusion control textile 252 and a skeleton 250 contacted by textile 252. Elongate catheter body 216 defines a longitudinal axis $A_2$, and may be functionally similar to catheter 14 described above. Catheter 214 may differ from catheter 14 with regard to the manner in which a fiber network 254 of textile 252 is constructed to impart a pressure sensitive flow rate property and a pressure insensitive flow distribution property, of a fluid emission profile of catheter 214. FIG. 6 includes several detailed enlargements, including a view of fiber network 254 at a proximal location, the leftmost detail view in FIG. 6; a distal location, the rightmost detail view in FIG. 6; and at a middle location. Rather than a woven textile, textile 252 may include a knitted textile having a plurality of fibers 270 in a knitted configuration. In further contrast to the embodiment described above, fibers 270 may include a non-uniform thickness which may also mean that fibers 270 have a non-uniform denier. Fibers 270 may have a relatively greater thickness in a proximal portion of textile 252, a relatively lesser thickness in a distal portion, and a medium thickness in a middle portion. It may further be noted that couplings 271 are shown between adjacent ends of fibers 270 having differing thicknesses. Couplings 271 may include joints where different thickness fiber strands are connected to one another such as by heat setting or tying, for example. The use of different thickness fibers 270, and in particular fibers having a distally attenuated thickness, results in a higher density space filling configuration of textile 252 at a proximal location versus a lower density space filling configuration at a distal location, and a medium density space filling configuration at a middle location.

Figure 7:
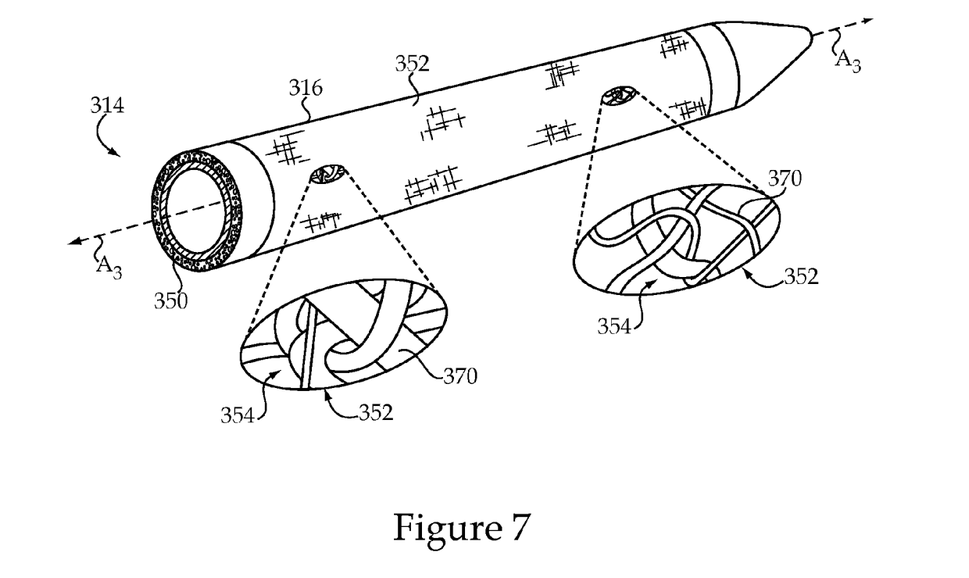
FIG. 7 is a partially sectioned perspective view, with detailed enlargements, of an infusion mechanism according to yet another embodiment.

Referring to FIG. 7, there is shown an infusion catheter 314 according to yet another embodiment. Infusion catheter 314 includes an elongate catheter body 316 defining a longitudinal axis $A_3$, and including a skeleton 350 and a porous infusion control textile 352. Textile 352 may include a fiber pattern characterized as "non-woven." The term non-woven is used herein in a manner consistent with its use in the field of textile engineering, and generally means that fibers 370 are not arranged in a regular pattern such as that attained via weaving or knitting. Textile 352 could include a felted textile. Textile 352 may further include differently sized fibers, differently shaped fibers, and fibers which do not loop about or otherwise engage with one another in any sort of regular pattern. It may be noted that in the leftmost, proximal detailed enlargement, fibers 370 include a relatively high density space filling configuration. Fibers 370 in the rightmost or distal detailed enlargement include a lower density space filling configuration. The different space filling configurations may result from different size fibers, different shaped fibers, different crowding among the fibers, a different geometric pattern among the fibers, or a combination of these and other factors, in a proximal portion versus a distal portion of textile 352. An adhesive or heat setting strategy may be used to cause fibers 370 to adhere to one another.

In view of the foregoing, it will be appreciated that a wide variety of different strategies may be used in designing textiles having the desired attributes described herein. In addition to the techniques described above, textiles might be manufactured for use with catheters where a fiber pattern changes proximally to distally, for instance a changing pattern of interlacing among fibers to result in a different density space filling configuration at different locations. In further embodiments, thermoplastic textile materials might be used such that fibers could be heated and deformed, by melting or partial melting, non-uniformly, squishing some material to a relatively more flat state in a proximal textile region while leaving other fibers unflattened in a distal textile region.

INDUSTRIAL APPLICABILITY

Figure 8:
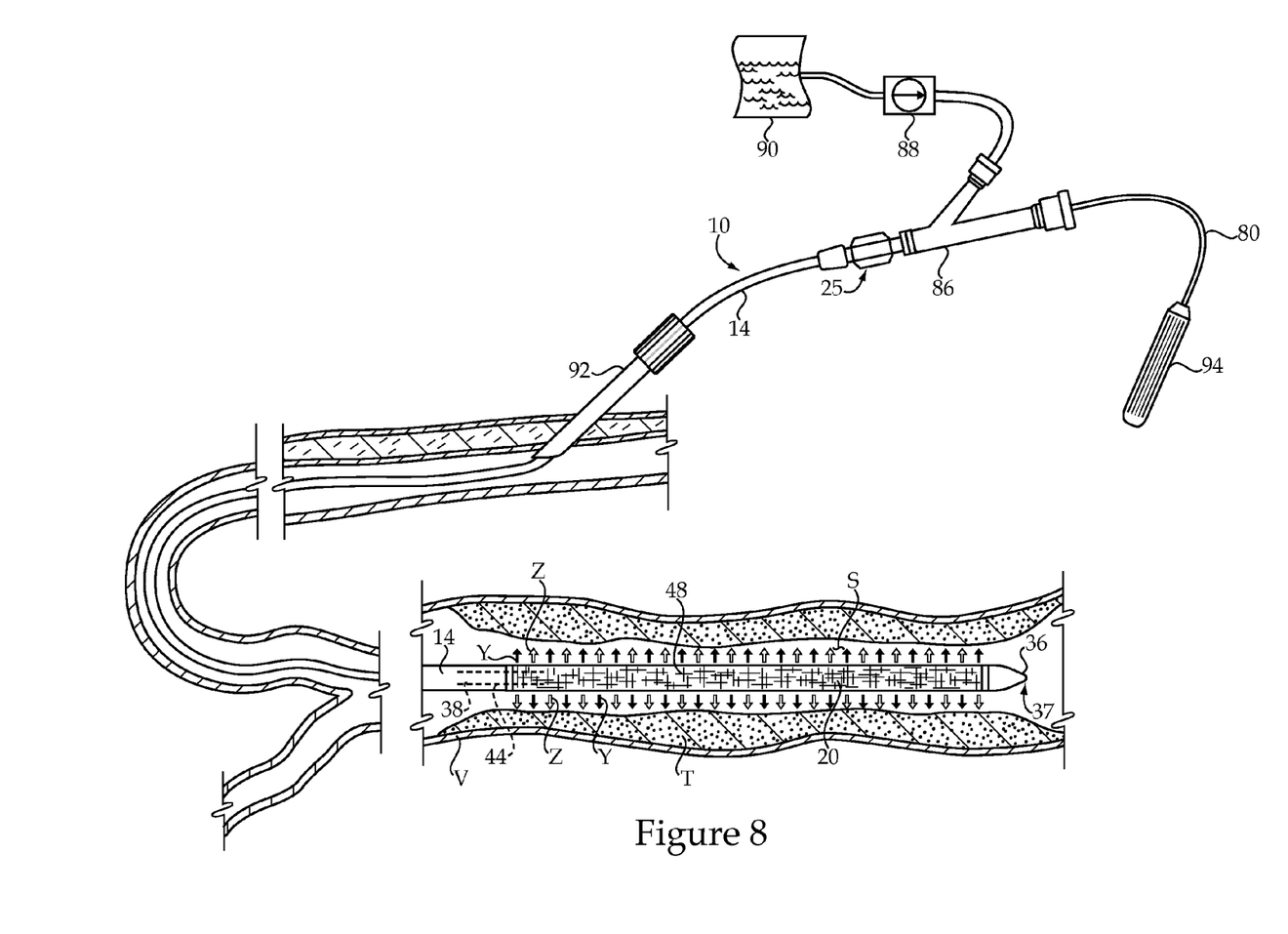
FIG. 8 is a pictorial view of an infusion mechanism, at one stage of an infusion procedure according to the present disclosure.

Referring to FIG. 8, there is shown infusion mechanism 10 as it might appear having been positioned for performance of an infusion procedure on a patient. Catheter 14 passes through an introducer 92 or the like and into a body lumen of a patient. The body lumen may include a vascular structure V such as a vein or artery. Catheter 14 is positioned such that distal body component 20 is located at a treatment site within vascular structure V, where a thrombus T has formed. Infusion lumen 44 is in fluid communication with an intraluminal space S by way of outlets 48.

In the configuration depicted in FIG. 8, a fitting 86 such as a Y-fitting is coupled with manifold 25 and fluidly connects catheter 14 with a reservoir 90 containing a treatment fluid such as a liquid thrombolytic agent by way of an infusion pump 88. Infusion pump 88 may be configured to continuously or periodically supply treatment fluid from reservoir 90 to fluid supply lumen 38, and thenceforth to infusion lumen 44 for conveying into intraluminal space S. In other embodiments, rather than an infusion pump, gravity feed or a pressure cuff coupled with reservoir 90 might be used. Wire guide 80 extends through fitting 86 and through lumen 38 and lumen 44. In the configuration depicted in FIG. 8, catheter 14 has been placed via over-the-wire placement at the treatment site, however, as discussed above alternative placement strategies are contemplated herein. A wire guide handle 94 is shown coupled with wire guide 80 and may be used to manipulate wire guide 80 in a conventional manner.

With infusion mechanism 10 positioned approximately as shown in FIG. 8, treatment fluid may be supplied from supply lumen 38 to infusion lumen 44, and the treatment fluid may be conveyed from infusion lumen 44 into the body lumen of the patient by way of outlets 48. As discussed above, a flow rate of treatment fluid from catheter 14 may be controlled in a manner which is responsive to a supply pressure of the treatment fluid. In the illustrated embodiment, supply pressure may be varied by controlling pump 88, for example. Controlling the supply pressure might include turning pump 88 on or off, or varying an outlet pressure of pump 88. In other embodiments, supply pressure might be controlled by actuating or adjusting a pressure cuff coupled with reservoir 90, or even by manually squeezing reservoir 90.

When catheter 14 is initially positioned at a treatment site within a patient, it may be understood to be in a rest state. The rest state may include a state at which fluid is not being conveyed from lumen 44 into intraluminal space S. Commencing supplying treatment fluid from supply lumen 38 to infusion lumen 44 may be understood to adjust catheter 14 from the rest state to an infusion state at which fluid is conveyed from lumen 44 to intraluminal space S. Adjusting catheter 14 from the rest state to the infusion state will typically occur subsequent to guiding catheter 14 to the treatment site. Infusion lumen 44 will typically fluidly connect with intraluminal space S in each of the rest state and the infusion state, in contrast to certain known infusion catheters where a valve mechanism is used to establish fluid communication between an infusion lumen and an intraluminal space only after the catheter has been positioned at a treatment site. As discussed above, distal outlet 37 may be partially or completely blocked during conveying fluid from infusion lumen 44 into intraluminal space S.

Adjusting catheter 14 from the rest state to the infusion state may occur by increasing a pressure of the treatment fluid within lumens 38 and 44. As noted above, this might occur by turning pump 88 on, or otherwise increasing a supply pressure of the treatment fluid to commence infusion. A set of solid arrows Y and a set of open arrows Z are shown in FIG. 8, each of which represents treatment fluid flowing from catheter 14 into intraluminal space S. As infusion commences, pressure within lumen 44 may rise sufficiently to overcome a fluid pressure in intraluminal space S such that treatment fluid begins to flow out of catheter 14. This initial state of infusion may occur at a first time, such as just after pump 88 is turned on or near the beginning of a pumping stroke. At the first time, flow rate of fluid from catheter 14 into intraluminal space S may be relatively low, corresponding to a relatively low pressure within lumen 44, which is in turn based on the supply pressure provided by pump 88. The number of arrows Y in FIG. 8 may be understood to illustrate the initial, relatively low flow rate, at the first time.

Following commencing infusion, pressure in lumen 44 may increase to a relatively higher pressure at a second, later time such as upon reaching a predefined outlet pressure with pump 88 or near the end of a pumping stroke of pump 88. In response, a relatively higher flow rate of fluid from catheter 14 into space S may occur. This relatively higher flow rate at the relatively higher supply pressure may be understood as illustrated by both arrows Y and arrows Z. In other words, a relatively higher flow rate is shown via a greater total number of arrows. It may thus be understood that a relatively lower flow rate may be associated with a relatively lower supply pressure, and a relatively higher flow rate may be associated with a relatively higher supply pressure. It may further be noted that each of arrows Y and Z are distributed relatively uniformly along an infusion length of catheter 14. At the relatively lower supply pressure, flow distribution of treatment fluid may be relatively uniform. At the relatively higher supply pressure, flow distribution may also be relatively uniform. Treatment fluid may be conveyed from catheter 14 into intraluminal space S continuously from the first time to the second time. When it is desired to end infusion, either at the end of the overall procedure or between intermittent periods of infusion, supply pressure may be reduced to a level where fluid is no longer urged out of catheter 14 into space S. To conclude the overall procedure, catheter 14 may be removed from the patient in a conventional manner.

By passing treatment fluid through a fiber network during conveying fluid as described herein, non-uniformity in a flow distribution pattern of treatment fluid during an infusion procedure may be reduced in comparison to that which would otherwise typically be expected. For instance, a catheter using a textile material which does not include the higher and lower density space filling configurations described herein would likely not be capable of uniformly distributing a treatment fluid into an intraluminal space, or would require some other, additional strategy to attain or approach uniformity. Catheter designs having still other materials such as conventional perforated plastic tubes typically have similar problems in uniformly distributing fluid, at least where no specialized design or mechanism for reducing non-uniformity is used. Since catheter 14 and other catheters contemplated herein can operate to infuse treatment fluid at a range of supply pressures without disturbing a desired flow distribution of the fluid, reducing non-uniformity in the flow distribution pattern may take place in a manner which is decoupled from the supply pressure. This means that supply pressure need not be so tightly controlled as is required in certain known designs, and a clinician is relatively free to vary infusion rate without concern for changing a distribution of treatment fluid from the catheter. Moreover, specialized internal catheter components for affecting flow distribution are unnecessary. Apart from basic geometry, materials and construction, control over flow distribution, and in particular uniformity or near uniformity in flow distribution, may be achieved according to the present disclosure without the need for valves, multiple internal fluid passages and/or distribution manifolds, or other components which are typically expensive and labor-intensive to manufacture.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. An infusion catheter comprising:
   an elongate catheter body defining a longitudinal axis extending between a proximal body component and a distal body component, the proximal body component including a proximal body outer surface and a proximal body inner surface, and the distal body component including a distal body outer surface, a distal body inner surface, and a tapered distal tip;
   the proximal body inner surface defining a fluid supply lumen extending between a supply lumen inlet and a supply lumen outlet, and the distal body inner surface defining an infusion lumen connecting with the fluid supply lumen and extending between an infusion lumen inlet and a plurality of infusion lumen outlets formed in the distal body outer surface;

the distal body component further having a skeleton, and a porous infusion control textile contacting the skeleton and including the plurality of infusion lumen outlets, the porous infusion control textile extending circumferentially about the longitudinal axis and defining a fluid emission profile of the infusion catheter;

the porous infusion control textile further including a fiber network extending between a proximal textile end and a distal textile end, the fiber network including interlaced fibers and having a space filling configuration which is substantially circumferentially uniform and axially non-uniform; and the space filling configuration is of a higher density of the interlaced fibers in a pattern of interlacing at the proximal textile end, a lower density of the interlaced fibers in the same pattern of interlacing at the distal textile end, and a medium density of the interlaced fibers in the same pattern of interlacing between the proximal and distal textile ends, and the fiber network defines a pressure sensitive flow rate property and a pressure insensitive flow distribution property, of the fluid emission profile.

2. The infusion catheter of claim 1 wherein the fiber network includes a distally attenuated crowding of the interlaced fibers, such that the interlaced fibers are relatively more tightly crowded in the higher density space filling configuration and relatively less tightly crowded in the lower density space filling configuration.

3. The infusion catheter of claim 2 wherein the skeleton includes a wire frame endoskeleton, and the porous infusion control textile includes at least one textile layer wrapped about the endoskeleton and extending at least one complete circumferential turn about the longitudinal axis.

4. The infusion catheter of claim 3 wherein the elongate catheter body further includes a first seal assembly located between the proximal body component and the distal body component, and a second seal assembly located between the distal body component and the distal tip.

5. The infusion catheter of claim 4 wherein the first seal assembly and the second seal assembly include a first bushing and a second bushing, respectively, and wherein the porous infusion control textile and the skeleton are sandwiched between the first bushing and the proximal body component within the first seal assembly, and the textile and the skeleton are sandwiched between the second bushing and the distal tip within the second seal assembly.

6. The infusion catheter of claim 2 wherein the fiber network is undular, and each of the interlaced fibers having radially outward undulations which each include a portion of the distal body outer surface, and radially inward undulations which each include a portion of the distal body inner surface.

7. The infusion catheter of claim 6 wherein the porous infusion control textile includes a woven textile and the interlaced fibers include a plurality of warp fibers and a plurality of weft fibers, and wherein the distally attenuated crowding is defined by a non-uniform crowding of at least one of the warp fibers and the weft fibers.

8. The infusion catheter of claim 6 wherein the pattern of interlacing is uniform throughout the infusion control textile.

9. The infusion mechanism catheter of claim 8 wherein the fibers have a greater denier at the proximal textile end and a lesser denier at the distal textile end.

10. The infusion catheter of claim 1 wherein the infusion lumen includes a common infusion lumen in fluid communication with each of the plurality of infusion lumen outlets, and wherein the porous infusion control textile further includes a distally incremented porosity defined by a spacing among the interlaced fibers comprising the fiber network.

11. An infusion catheter comprising:
an elongate catheter body defining a longitudinal axis extending between a proximal body component and a distal body component, the proximal body component including a proximal body outer surface and a proximal body inner surface, and the distal body component including a distal body outer surface, a distal body inner surface, and a tapered distal tip;

the proximal body inner surface defining a fluid supply lumen extending between a supply lumen inlet and a supply lumen outlet, and the distal body inner surface defining an infusion lumen connecting with the fluid supply lumen and extending between an infusion lumen inlet and a plurality of infusion lumen outlets formed in the distal body outer surface;

the distal body component further having a skeleton, and a porous infusion control textile contacting the skeleton and including the plurality of infusion lumen outlets, the porous infusion control textile extending circumferentially about the longitudinal axis and defining a fluid emission profile of the infusion catheter; and the porous infusion control textile further including a fiber network extending between a proximal textile end and a distal textile end, the fiber network having a space filling configuration which is substantially circumferentially uniform and axially non-uniform, such that the space filling configuration is of a higher density at the proximal textile end, a lower density at the distal textile end, and a medium density between the proximal and distal textile ends, and the fiber network defines a pressure sensitive flow rate property and a pressure insensitive flow distribution property, of the fluid emission profile;

wherein the infusion lumen includes a common infusion lumen in fluid communication with each of the plurality of infusion lumen outlets, and wherein the porous infusion control textile further includes a distally incremented porosity defined by a non-uniform thickness among fibers comprising the fiber network.

* * * * *